United States Patent
Talish et al.

(10) Patent No.: US 6,261,249 B1
(45) Date of Patent: *Jul. 17, 2001

(54) ULTRASONIC TREATMENT CONTROLLER INCLUDING GEL SENSING CIRCUIT

(75) Inventors: Roger Talish, Hillsborough; Thomas Koscica, Clark, both of NJ (US); Alan Winder, Westport, CT (US); Emery Rose, Astoria, NY (US)

(73) Assignee: Exogen Inc., Piscataway, NJ (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/040,157

(22) Filed: Mar. 17, 1998

(51) Int. Cl.[7] ................................... A61B 17/56
(52) U.S. Cl. ............................... 601/2; 600/459
(58) Field of Search ............... 601/2; 600/9, 15, 600/437, 459; 607/7, 50, 51

(56) References Cited

U.S. PATENT DOCUMENTS

| 4,441,486 | 4/1984 | Pounds . |
|---|---|---|
| 4,530,360 | 7/1985 | Duarte et al. . |
| 4,708,127 | 11/1987 | Abdelighani . |
| 5,003,965 | 4/1991 | Talish et al. . |
| 5,184,605 | 2/1993 | Grzesykowski . |
| 5,186,162 | 2/1993 | Talish et al. . |
| 5,211,160 | 5/1993 | Talish et al. . |
| 5,269,306 | 12/1993 | Warnking et al. . |
| 5,314,401 | 5/1994 | Tepper . |
| 5,415,167 | 5/1995 | Wilk . |
| 5,520,612 | 5/1996 | Winder et al. . |
| 5,541,489 | 7/1996 | Dunstein . |
| 5,556,372 | 9/1996 | Talish et al. . |
| 5,699,803 | * 12/1997 | Carodiskey et al. .............. 600/459 |

FOREIGN PATENT DOCUMENTS

| 2 303 552 | 2/1997 | (GB) . |
|---|---|---|
| WO 88/02250 | 4/1988 | (WO) . |

* cited by examiner

Primary Examiner—Marvin M. Lateef
Assistant Examiner—Ali M. Imam
(74) Attorney, Agent, or Firm—Dilworth & Barrese

(57) ABSTRACT

A controller for driving an ultrasonic transducer is disclosed and includes a processor, responsive to a feedback signal, for generating control signals to an output driver which is responsive to the control signals, to cause the ultrasonic transducer to generate ultrasound having a power level corresponding to the control signal. The controller is preferably attached to a sensing circuit to determine the amount of ultrasound conductive gel associated with the ultrasonic transducer, and for generating the feedback signal therefrom. The controller includes data logging capabilities to record treatment data and prevent unnecessary extended treatment. The controller creates an environment for safer ultrasonic self-treatment by patients. The microprocessor used in the controller can be used to warn of a low battery condition or insufficient amount of ultrasound conducting gel. It can limit the usage of the transducer to prevent over treatment by comparing use data with acceptable limits and disabling the transducer if the limits have been exceeded. The device is contemplated to be portable for ease of transport by patients.

22 Claims, 8 Drawing Sheets

ULTRASONIC TREATMENT CONTROLLER INCLUDING GEL SENSING CIRCUIT

BACKGROUND OF THE INVENTION

1. Field of the Invention

This disclosure relates to the generation of ultrasound signals and, more particularly, to an ultrasonic controller for use with an ultrasonic transducer to accelerate the process of healing in both hard and soft tissue.

2. Description of the Related Art

The therapeutic value of ultrasonic waves is known. Various techniques and devices are used to apply ultrasound waves to various areas of the body. In one known technique a pulsed radio-frequency ultrasonic signal applied via a transducer to the skin of a patient and is directed to the site of the wound. The radio-frequency signal is in the range of 1.3 to 2 MHZ, and it consists of pulses at a repetition rate of 100 to 1000 Hz, with each pulse having a duration in the range of 10 to 20,000 microseconds. See, e.g. U.S. Pat. No. 4,530,360 to Duarte and U.S. Pat. No. 5,520,612 to Winder et al.

U.S. Pat. Nos. 5,003,965 and 5,186,162 both to Talish and Lifshey ("Talish '965" and "Talish '162", respectively) describe an ultrasonic delivery system where the R-F generator and transducer are both part of a modular applicator unit that is placed at the skin location. The signals controlling the duration of ultrasonic pulses and the pulse repetition frequency are generated apart from the applicator unit. Talish '965 and Talish '162 also describe fixture apparatus for attaching the applicator unit so that the operative surface is adjacent the skin location. In Talish '965 and Talish '162, the skin is surrounded by a cast, while in U.S. Pat. No. 5,211,160 to Talish and Lifshey ("Talish '160") fixture apparatus is described for mounting on uncovered body parts (i.e., without a cast or other medical wrapping). Talish '160 also describes various improvements to the applicator unit. Duarte, Talish '965, Talish '162 and Talish '160, are all incorporated into this application by reference.

As ultrasonic self-treatment becomes more popular, a need arises to make ultrasonic delivery systems easier and more convenient to use. Current ultrasonic transducers for home use create opportunities for the patient, participating in self-treatment, to make errors in time of exposure or improperly setting up the apparatus, for example, inadequate amounts of ultrasound coupling gel being used on the interface between the ultrasound transducer and the skin over the region where the defect exists. A daily 20 minute treatment session has been established as effective in accelerating healing of certain bone fractures. The effects of longer treatment are usually of no benefit to the patient. However patient compliance is necessary in order for the true benefits of ultrasound treatment to be realized. Therefore, self-treatment programs should be monitored and controlled.

Rigidly adhering to a 24 hour delay between treatment sessions often puts an unrealistic constraint on a patient with a self administrated treatment device. Non-routine occurrences or unexpected events often interfere forcing a patient to advance or delay treatment rather than skip the treatment session. A contiguous 20 minute session is preferred for each treatment with ultrasound, however, this period can be interrupted by common everyday events, for example, the door bell ringing. Therefore, a need exists for a treatment system that allows a patient to advance or delay treatment and which automatically prevents any unnecessary over treatment. There also exists a need to provide the flexibility to stop a treatment session and start up again within a reasonable time, with automatic protection against over treatment.

In order for a treatment session to be beneficial to a patient, at least a portion of the ultrasound wave must penetrate the body and reach the injury to accelerate the healing process. In order to minimize excessive attenuation of the ultrasound waves produced by the transducer, an ultrasonic wave coupling material, e.g. a conductive gel, is used between the surface of the skin and the transducer head. If an inadequate amount of gel is used or it is improperly applied by the patient to herself, the treatment session will not be as effective as it should be. Therefore, a need exists for determining whether or not a gel layer is properly applied or even if the patient forgets to apply the gel before treatment.

Ultrasonic treatment systems are made up of many components. Variations in component tolerances in the output driver circuitry or the output transducer, for example, create a need to perform minor adjustments to the output power level in order to achieve the required level of compliance. Although a manual tuning component traditionally works, its use requires a labor intensive process which can raise the cost of the final product. Therefore, a need to reliably set power levels and perform minor adjustments for ultrasonic transducers exists.

Patients often forget to keep and maintain accurate treatment logs. The duration of each treatment session and the time interval between treatments can prove to be important information for a treating physician or a patient. It would be advantageous to have a device that was capable of logging time efficiently and accurately to create a cumulative treatment history without relying on the patient to keep appropriate records.

SUMMARY OF THE INVENTION

A controller for driving an ultrasonic transducer is disclosed and includes a processor, responsive to a feedback signal, for generating control signals to an output driver which is responsive to the control signals, to cause the ultrasonic transducer to generate ultrasound having a power level corresponding to the control signal. The controller is preferably attached to a sensing circuit to determine the presence of a sufficient amount of ultrasound conductive gel associated with the ultrasonic transducer, and for generating the feedback signal therefrom. The controller includes data logging capabilities to record treatment data and prevent inappropriate treatment delivery. The processor creates the desired operating frequency.

The controller creates an environment for a simple, safe and efficient ultrasonic self-treatment by patients. The microprocessor used in the controller creates the operating frequency and can warn of a low battery condition or insufficient amount of ultrasound conducting gel. It can limit the usage of the transducer to prevent over treatment by comparing use data with acceptable limits and disabling the transducer if the limits have been exceeded. It can also be used as a switching regulator to improve lithium battery life. The device is contemplated to be portable for ease of transport by patients and can be configured for use with a wide variety of power supplies at a number of different anatomical treatment sites.

An ultrasound delivery controller system for driving ultrasonic transducers includes a plurality of controller boards, each board for controlling an ultrasound transducer wherein one of the plurality of boards is a master board for controlling and sequencing the other boards.

BRIEF DESCRIPTION OF DRAWINGS

The invention will be described in detail in the following description of preferred embodiments with reference to the following figures wherein.

DETAILED DESCRIPTION OF PREFERRED EMBODIMENTS

The present invention includes the use of a microprocessor to receive and output electrical signals from a feedback circuit and to an ultrasonic transducer. The microprocessor can receive signals from a sensing circuit and produce a warning sign to the user of the ultrasonic treatment device. The microprocessor can be used to log treatment times and intervals between treatments. The microprocessor can also be used to output varying power levels to the ultrasonic transducer. A compliance indicator may also be provided to, inter alia, inform the patient as to whether they have been complying with the prescribed treatment regimen. The microprocessor can be input with treatment, use and/or control parameters to facilitate, e.g., compliance, return and/or disabling of the unit. For example, the microprocessor can be programmed for 1 treatment sequence, two or more sequences or an unlimited number of sequences. The microprocessor can also limit the number of times per day the unit can be used to avoid potential misuse. Further details are described herein.

Figure 1:
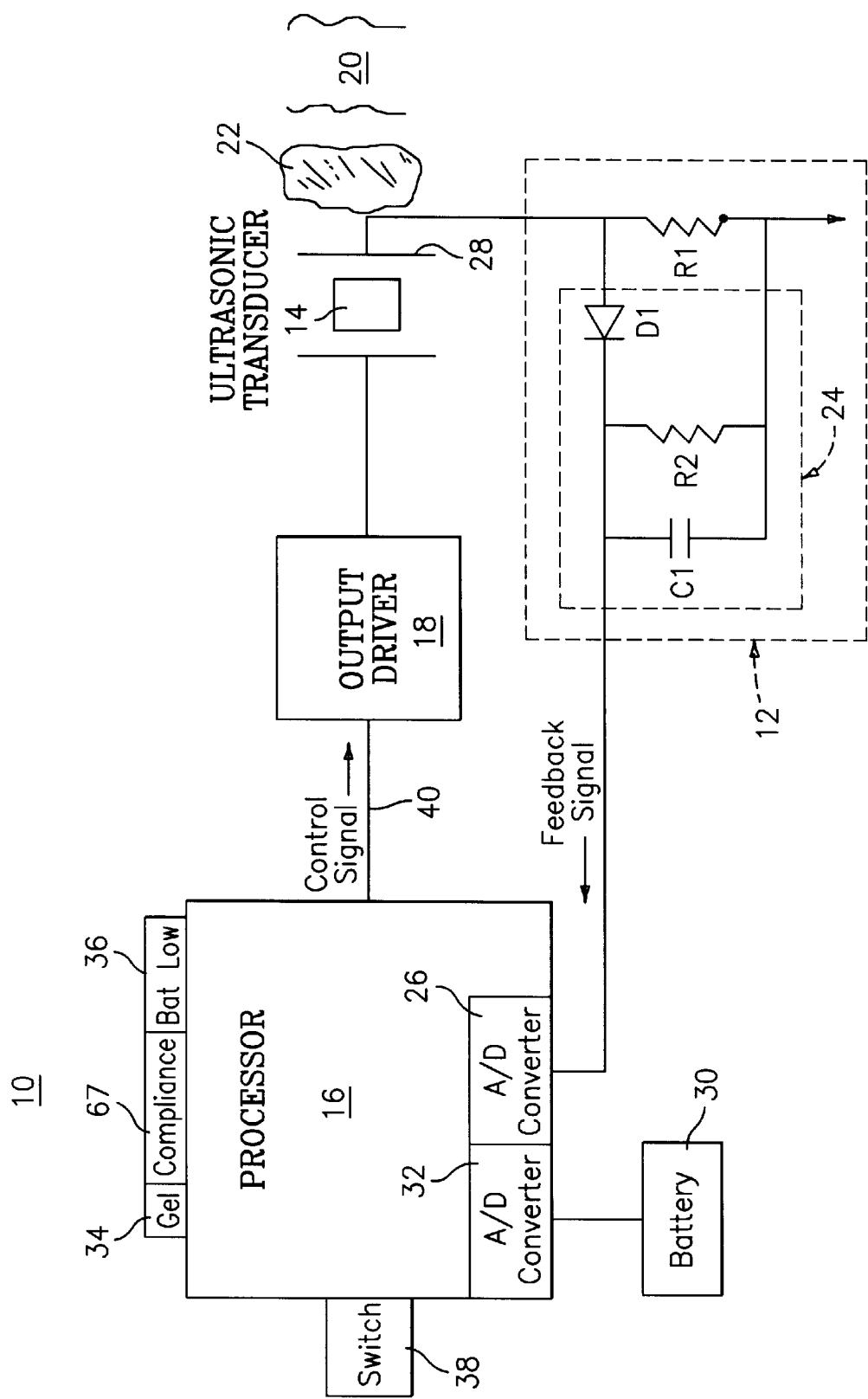
FIG. 1 is a schematic diagram of an ultrasonic transducer controller with an AC current detector connected to an ultrasonic transducer.

Referring now in specific detail to the drawings, with like reference numerals identifying similar or identical elements, FIG. 1 shows a schematic diagram of an ultrasonic transducer controller 10 with an AC current detector circuit 12 connected to an ultrasonic transducer 14. The transducer controller includes a processor 16, which could be a microprocessor used in conjunction with an ultrasonic transducer 14. The processor 16 generates control signals which are amplified by an output driver 18 to the desired power level and imparted to the ultrasonic transducer 14. A preferred transducer could be an air backed quarter wave matched transducer.

The delivery of ultrasound to a target 20 requires an efficient coupling path between the transducer and the patient's skin and soft tissue. A material for ultrasound coupling is used, typical characteristics include coupling, hypoallergenic composition and slow to dry. Commonly used materials are sonically conductive materials, such as glycerol, water, oils, lotions, etc. A layer of gel 22 is preferred and often used to effect a proper interface for propagating ultrasonic waves 24 into the body 20. The application of gel to the surface of an ultrasonic transducer changes the acoustic load impedance on the transducer such that the electrical current flowing through the transducer tends to be reduced. If gel is absent or present in an insufficient amount, the current through the transducer will be excessive. Thus, the amount of current flowing through the transducer can be used as an indicator as to whether gel is available to couple the ultrasonic waves through the interface between the transducer and the patient's body. Conversely, if no current is flowing (zero current) then there may have been a malfunction of the transducer or more often of a cable or connection to the transducer. Also, because ultrasound is reflected from the gel/tissue media, a receiver can be used to sense reflected ultrasound signals. If little or no reflected signal is received, an insufficient gel signal can be given.

The detector circuit 12 is in series with the transducer 14. A current sensing resistor R1 is connected between a transducer side which contacts a patient's skin and electrical common. When current flows through the transducer, it induces a proportional but small voltage across the current sensing resistor R1. This voltage will be referenced to common since the current sensing resistor R1 is connected to electrical common. The current sensing function of R1 can be performed with either an inductor or a capacitor to provide an equivalent impedance magnitude as R1. Whereas the resistor is dissipative, the inductor or capacitor is nearly without loss. This has the advantage of saving battery power.

The current sensing resistor R1 is wired in parallel with a peak detector circuit 24. The peak detector circuit 24 includes a diode D1 in series with a capacitor C1 and resistor R2 which are in parallel with one another. The peak detector circuit 24 is also referenced to common. The purpose of the peak detector circuit 24 is to rectify the periodic alternating voltage across the current sensing resistor R1. The alternating signal is filtered and a proportional DC magnitude is derived. The diode D1 rectifies the signal, capacitor C1 smooths the DC signal and resistor R2 discharges C1 when there is no signal on R1. The equivalent function of R2 can be performed in the processor 16 if the A/D sense port for A/D converter 26 can be selectively changed to a digital ground to discharge C1. The DC signal's magnitude can be sampled by the processor 16 to determine if adequate gel is present or if the transducer 14 is not functioning. One method of detection includes the conversion of the analog DC magnitude, or the feedback signal, into a digital value through the use of an analog to digital converter 26 (herein A/D converter). The A/D converter 26 is shown integrated with the processor 16. Alternately, the A/D converter 26 can be placed on a printed circuit board (not shown) along with other components of the processor 16. The software code is preferably encrypted for security.

The feedback signal is read from a connection point between the diode D1 and C1 of the peak detector circuit. The feedback signal is proportional to the transducer current and is a function of the motional impedance of the transducer which varies as a function of the acoustic impedance at the face of the transducer 28. The processor 16 senses the acoustic impedance through the analog to digital conversion from the current detector circuit 12. The motional impedance will be lowest with good skin contact at the face of the transducer. If an unsatisfactory acoustic coupling is detected, the user is given an indication by means of an alarm, for example a light emitting diode 34 on the unit next to the word "GEL".

Figure 1A:
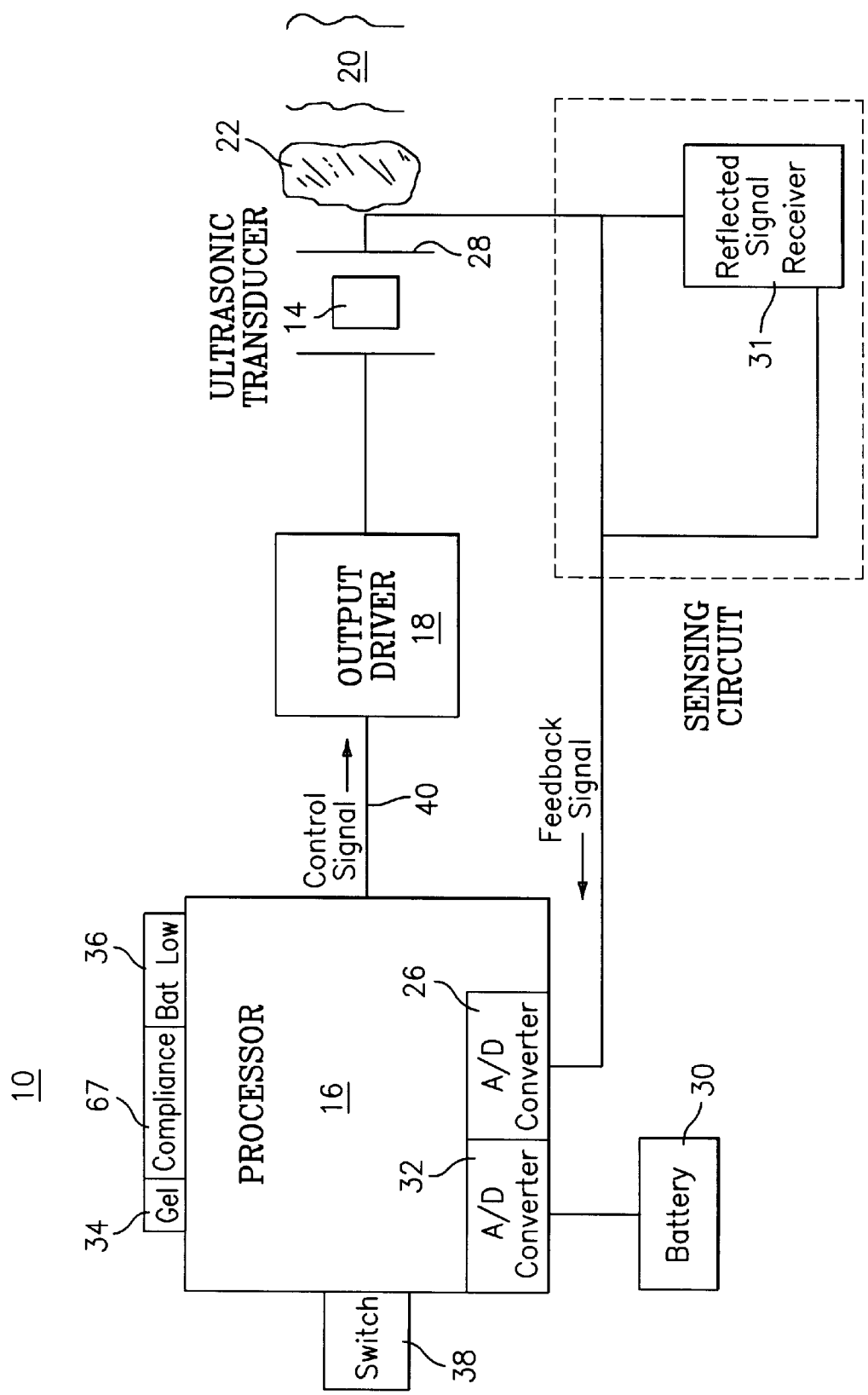
FIG. 1A is a schematic diagram of an ultrasonic transducer controller with a reflected signal receiver connected to an ultrasonic transducer.

FIG. 1A shows an alternative embodiment of the gel sensing means wherein a reflected signal receiver 31 is used to receive a reflected portion of an ultrasound signal. If a reflected signal of insufficient magnitude is received, a low gel warning is generated and the signal can be suspended.

It is desirable to have a portable ultrasonic transducer so that the patient who is self-treating can have the unit available wherever they are. With this in mind, a processor or microprocessor 16 and transducer 14 can be powered by an energy storage device 30, such as a battery. It is therefore necessary to give a patient warning when the energy storage device runs low. A similar scheme can be used as before. For example, the power from the energy storage device 30 is sampled. The value of the voltage is converted from an analog signal to a digital signal by means of an A/D converter 32. The digital signal can be compared to a predetermined value stored in the memory of the microprocessor 16. If the energy source is low an alarm is activated, such as a liquid crystal display 36, indicating "Bat Low", for example, or a light emitting diode.

The transducer controller can be activated by a switch 38 or a button located on or near the processor.

Figure 2:
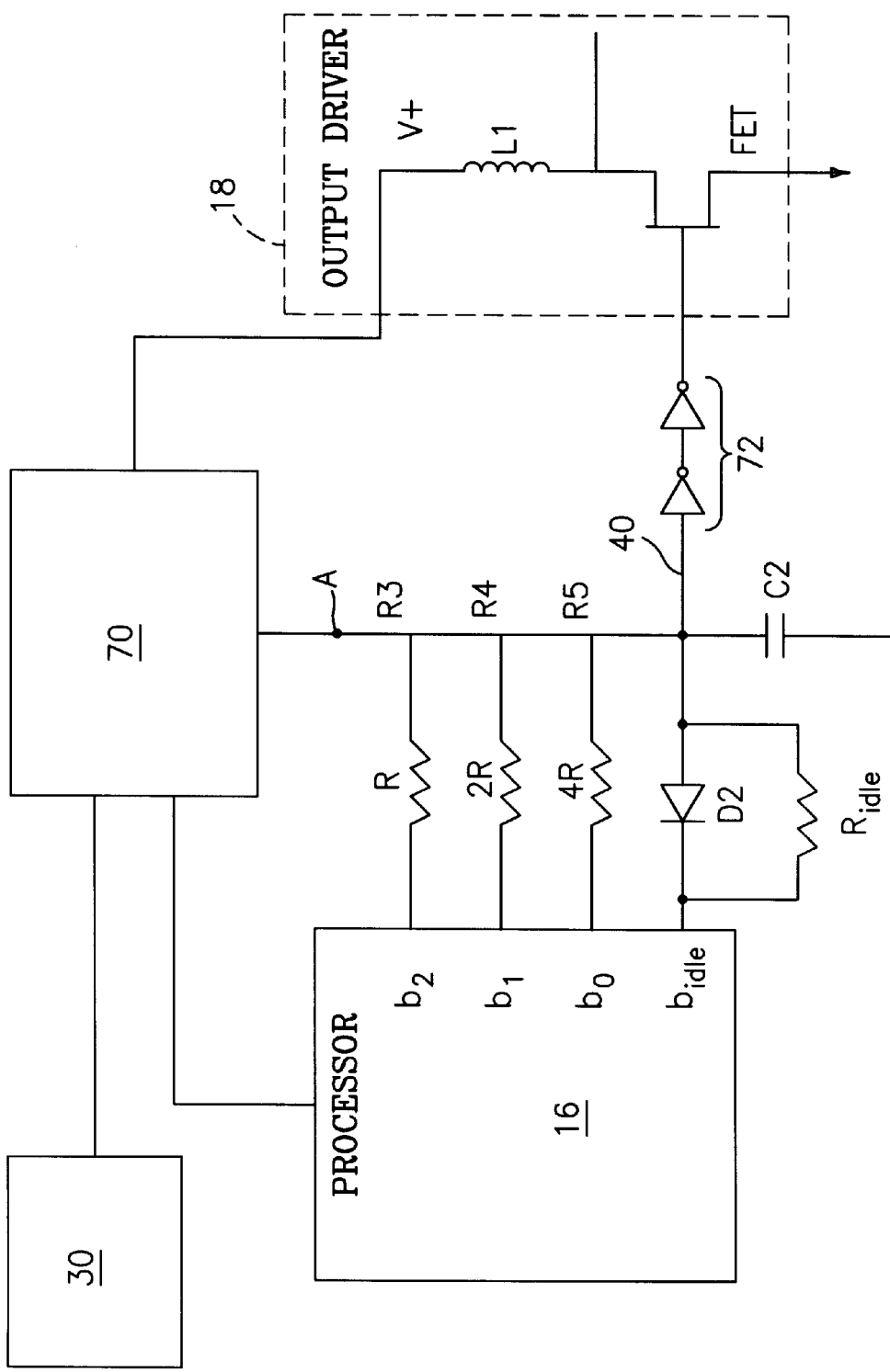
FIG. 2 is a schematic of the transducer controller with digital output ports connected to an output driver.

FIG. 2 is a schematic of the transducer controller 10 with digital output ports connected to an output driver 18. Output bits $b_0$, $b_1$, and $b_2$ can be generated by the microprocessor 16 or stored in the microprocessor's memory for retrieval at the appropriate time. The bits represent a high or low voltage ("1" or "0", respectively). Output bits $b_0$, $b_1$ and $b_2$ are passed through resistors having a magnitude proportional to the bits place value, thereby creating more current for a given bit value of "1". For example a "high" bit on line $b_3$ generates a current proportionally greater than a "high" on line $b_1$ because the resistance in the line is greater at $b_1$. The resistors, R3, R4, R5 and diode D2 are connected to the same node, or control signal line 40, to produce an ultrasound control signal proportional to the output bits. The control signal line is connected to common through a capacitor C2. The control signal line current can be varied by the line resistances R3, R4 and R5 which set the charging rate of the capacitor C2. $R_{idle}$ sets a minimum charge rate. C2 drives the voltage in the control signal line 40 which is then amplified by an output driver 18. Different charge rates of capacitor C2 create varied power levels in the transducer 14 once the signal is amplified. The amount of variation of the signal can be controlled by the word size at the output of the controller. For example, if the word has three bits $b_0$, $b_1$, and $b_2$ and each bit has a possible value of high or low then 23 or 8 possibilities exist. For "N" bit words $2^N$ possibilities exist. To use "N" bits requires "N" digital ports with weighted resistors. A possible output bit pattern creating 8 distinct power levels is shown in TABLE 1, below, for a digital word. The control signal is obtained by cyclically alternating between the codes for "ON and "OFF" at an ultrasonic carrier frequency. Note, that an idle pin, $b_{idle}$, is always driven cyclically.

Larger words may be implemented by adding more outputs ($b_3$, $b_4$, etc.) from the processor 16. More resistors may be connected to these additional output with magnitudes adjusted by a factor of 2, for example, R/2, R/4, etc.

TABLE 1

| Power Level | ON Output Bits $b_2\ b_1\ b_0\ b_{idle}$ | OFF Output Bits $b_2\ b_1\ b_0\ b_{idle}$ |
|---|---|---|
| 0 (Low Power) | 000 1 | 000 0 |
| 1 | 001 1 | 000 0 |
| 2 | 010 1 | 000 0 |
| 3 | 011 1 | 000 0 |
| 4 | 100 1 | 000 0 |
| 5 | 101 1 | 000 0 |
| 6 | 110 1 | 000 0 |
| 7 (High Power) | 111 1 | 000 0 |

The control signal must be amplified prior to being applied across the transducer 14. Any stable AC voltage amplifier providing a gain in the range of about 3 to 5 and capable of driving a 50 Ω load is possible. In one embodiment, the amplifier could contain a Field Effect Transistor (FET) having its gate coupled to the control signal line 40. Diode D2 can be connected between the $b_{idle}$ bit output and an end of the capacitor C2 opposite the common connection. D2 would allow for a fast discharge of C2 once a predetermined time has elapsed which may be determined by the digital bits cyclically switching to OFF. This would disable the output driver 18 and, therefore, the transducer.

A switching regulator 70 may be connected to L1 of the output driver 18 and the resistors at a node A. The switching regulator 70 is powered by battery 30 and controlled by the processor 16, i.e., turned on for treatment and off for sleep. The switching regulator 70 enables the use of any size battery because the output voltage supplied, $V_{variable\ supply}$, can be regulated. Thus, alkaline batteries, etc. can be used. Typical batteries provide 6–12 volts. Using the regulator allows the battery voltage to be adjusted to a higher value, for example, 10–15 volts. This enables a higher voltage to be supplied to the output driver 18 for ultrasound treatment. The output of switching regulator 70 may be set by adjusting the values of the resistors R3–R5, for example.

Figure 3:
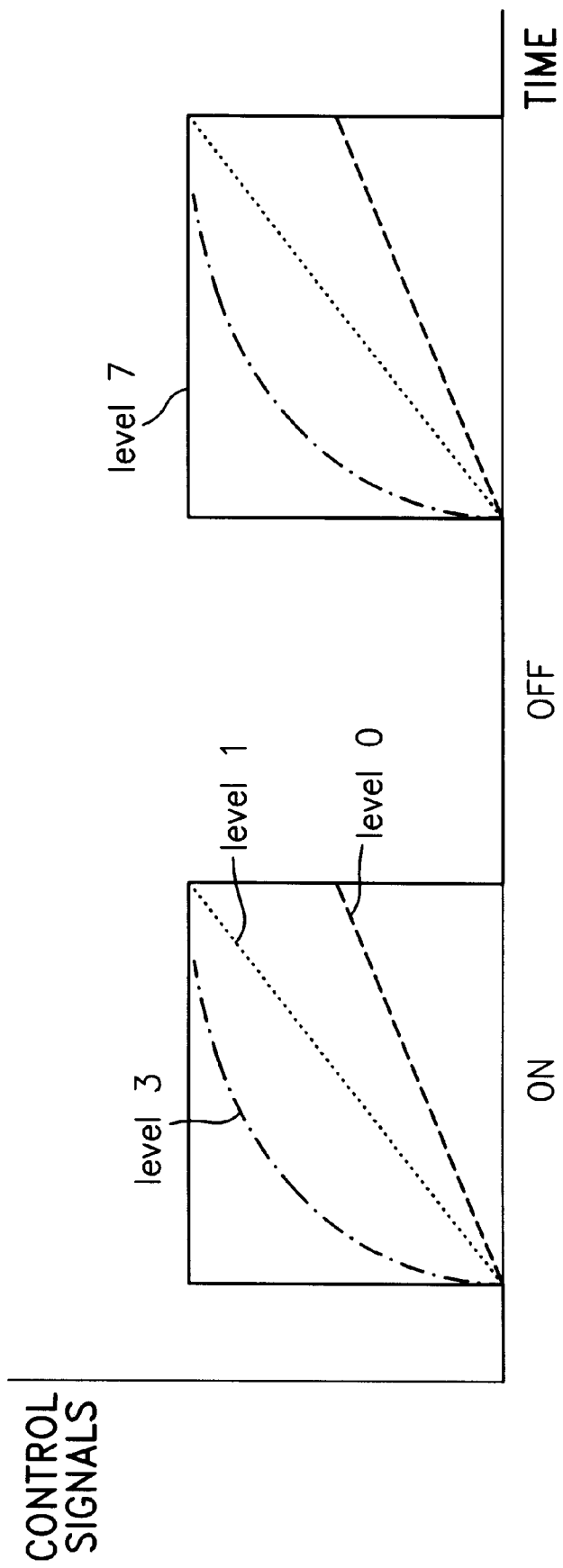
FIG. 3 is a time plot of several control signals corresponding to different power levels with a constant duty cycle.

In a preferred embodiment, a CMOS digital buffer 72 may be included. The buffer 72 includes two invertors which are connected in-line on the control signal line 40. Control signal line 40 connects to the FET of the output driver 18. The buffer 72 increases the switching efficiency of FET. The buffer switches from low to high when the control signal amplitude as shown in FIG. 3 rises to approximately 50% full amplitude and off when falling below approximately 50% control signal amplitude. In this manner, the slowly rising control signals in FIG. 3 are converted to a pulse width modulated square wave drive signal for the FET. The buffer 72 is more temperature stable since it comprises CMOS transistors and reduces the temperature dependency of the FET for switching the output driver 18 on and off. This is advantageous in a battery powered system since battery power is conserved in efficiently switched systems.

In another embodiment, the sensing circuit can provide an estimate of and control the input power to the transducer 14. The circuit includes a current sensor, a voltage sensor, a multiplier and an averaging circuit, such as a low pass filter. The analog power estimate at the output of the averager is converted to a digital signal by means of the A/D converter 26 in the processor 16. This digital value can then be compared to a stored reference and the differential used to adjust the control signal to the FET of the output driver, thereby controlling the acoustic power output of the transducer to within prescribed limits.

FIG. 3 shows a time plot of several control signals corresponding to a given output power level. The power level numbers correspond to the example outlined in TABLE 1, above. The highest power level, 7, is achieved by the fastest charge up of capacitor C2. Hence the steep leading edge of control signal 7 when plotted verses time. The y-axis represents voltage, for example, and is limited by the capacitor C2 and other circuit parameters. The maximum voltage is achieved quickly when the largest charging current corresponding to the highest bit word value is encountered. For intermediate power settings charging the capacitor is delayed resulting in a shorter duty cycle as shown in FIG. 3.

Figure 4:
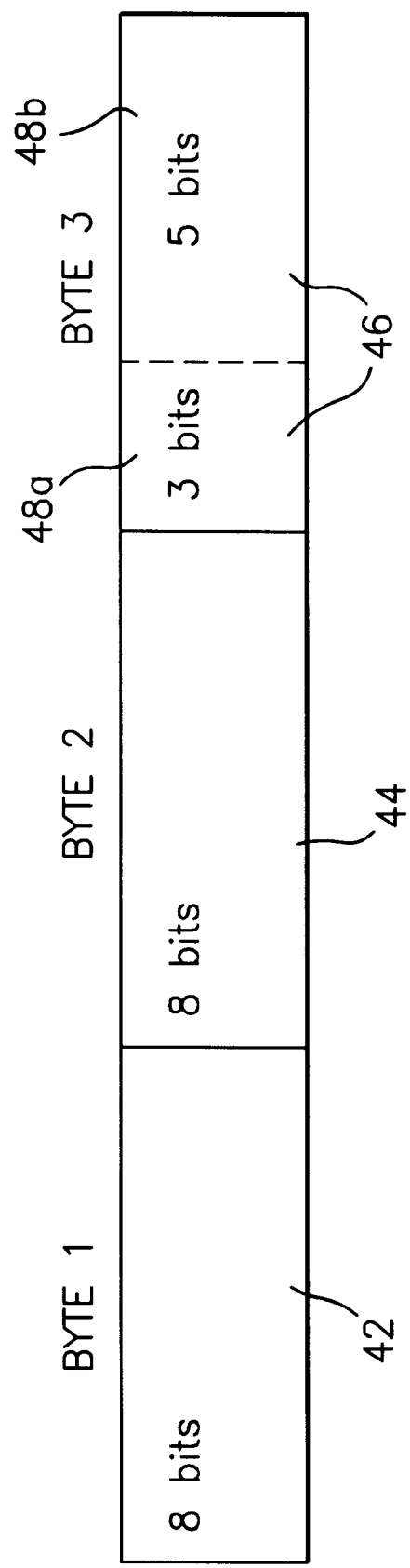
FIG. 4 illustrates a memory allocation scheme for recording the time of treatment and the interval between treatments.

The processor 16 has the capability of memory storage. FIG. 4 demonstrates a memory allocation scheme for recording the time of treatment and the interval between treatments. An optimized daily treatment time has been shown to be a consistent 20 minute session. The effects of longer daily treatments (over 20 minutes per session) are not in the overall treatment plan for a patient. Therefore, a mechanism for ensuring correct treatment time is desirable. Information recording can be employed through processor memory. An electrically erasable programmable read only memory (EEPROM) device (not shown) could be used, for example. Each recorded entry consists of 3 bytes or 24 bits of memory. A first byte (8 bits) would contain the number of whole days that have elapsed since the previous treatment. Eight (8) bits allow the storage of an integer numbers form 0 to 255. If the number of days exceeds 255 than it can be recorded as 255. This can also be used as an indicator to disable the unit after a set number of days. For example if treatment is to be for 3 weeks, a limit of 21 may be used in conjunction with a rule in software to disable the unit.

A second byte 44 and part of a third byte 48a (11 bits) can be used to store the number of minutes that have elapsed since the last treatment. Eleven (11) bits are capable of storing an integer from 0 to 2047. Since there are only 1440 minutes in a day, only the integers 0 to 1439 are needed in these bits. In this way the number of days and minutes is recorded since the last treatment session. The remaining five (5) bits of the 24 would represent the amount of time in minutes of a given session. The five bits can contain an equivalent binary number from 0 to 31, of which only 0 to 20 would be needed since the time of the session would be monitored by software to automatically end the session at 20 minutes.

The data collected by the processor 16 can be used to not only log the patient's treatment, but also to prevent the patient from extending the treatment. A first counter (not shown) is provided in the processor that allows a patient to reinitiate a session that has been interrupted. Once a patient begins a new 20 minute treatment session, a four hour clock is started. If the patient is interrupted during the session the remaining treatment time remains available to continue treatment within the four hour time limit. When the four hour time period expires the patient can no longer receive treatment and the remaining time left in the session is no longer available. For example, a patient begins a new 20 minute treatment session, after 10 minutes the patient is interrupted. The remaining ten minutes of treatment must be used within the next 3 hours and 50 minutes or that treatment time is lost. To prevent excessive treatment, a minimum of 12 hours must lapse between treatment sessions, but 2 treatment sessions should not occur within the same 36 hour period. Counters (not shown) on the processor can keep track of treatment frequency and disable the transducer if the patient attempts treatment sessions within the 12 hour period or 2 times in 36 hours. For example, if a patient desires to move up a treatment session by 12 hours from the normally prescribed 24 hour period, it is possible. However, he must wait 24 hours before the next treatment can be performed to satisfy the requirement of a maximum of 2 sessions per 36 hour period.

A further use for the processor includes providing a means for defining the number of treatments a given unit can perform without being recharged or reprogrammed. In one embodiment, a unit is programmed using an EEPROM, which does not require battery power, to store a set number of sessions or the total amount of time available to the patient. Different types of injuries may require a different number of treatment sessions. By using an electronic key (input code) or a smart battery (a battery which identifies itself by an input code) the processor 16 could be enabled. However, when the number of allocated minutes or number of sessions expires the electronic key is erased disabling the circuit. In the case of the smart battery, it is necessary to prevent the patient from switching the battery with a different battery having the same electronic key which would allow more treatments or renew the amount of time on the unit. In other words switching the battery should not refresh the unit to allow more time or sessions. This enablement feature allows sale of treatment minutes rather than the sale of the actual equipment.

The processor may also include programming which requires prepayment prior to activation or payment prior to or contemporaneous with a treatment or sequence of treatments. This feature could facilitate return of the unit and avoid potential unauthorized use. Similarly, an end-of-file disabling program can be provided which inactivates/ disables the unit after a predetermined number of uses and/or the passage of a predetermined time period.

Figures 5, 6:
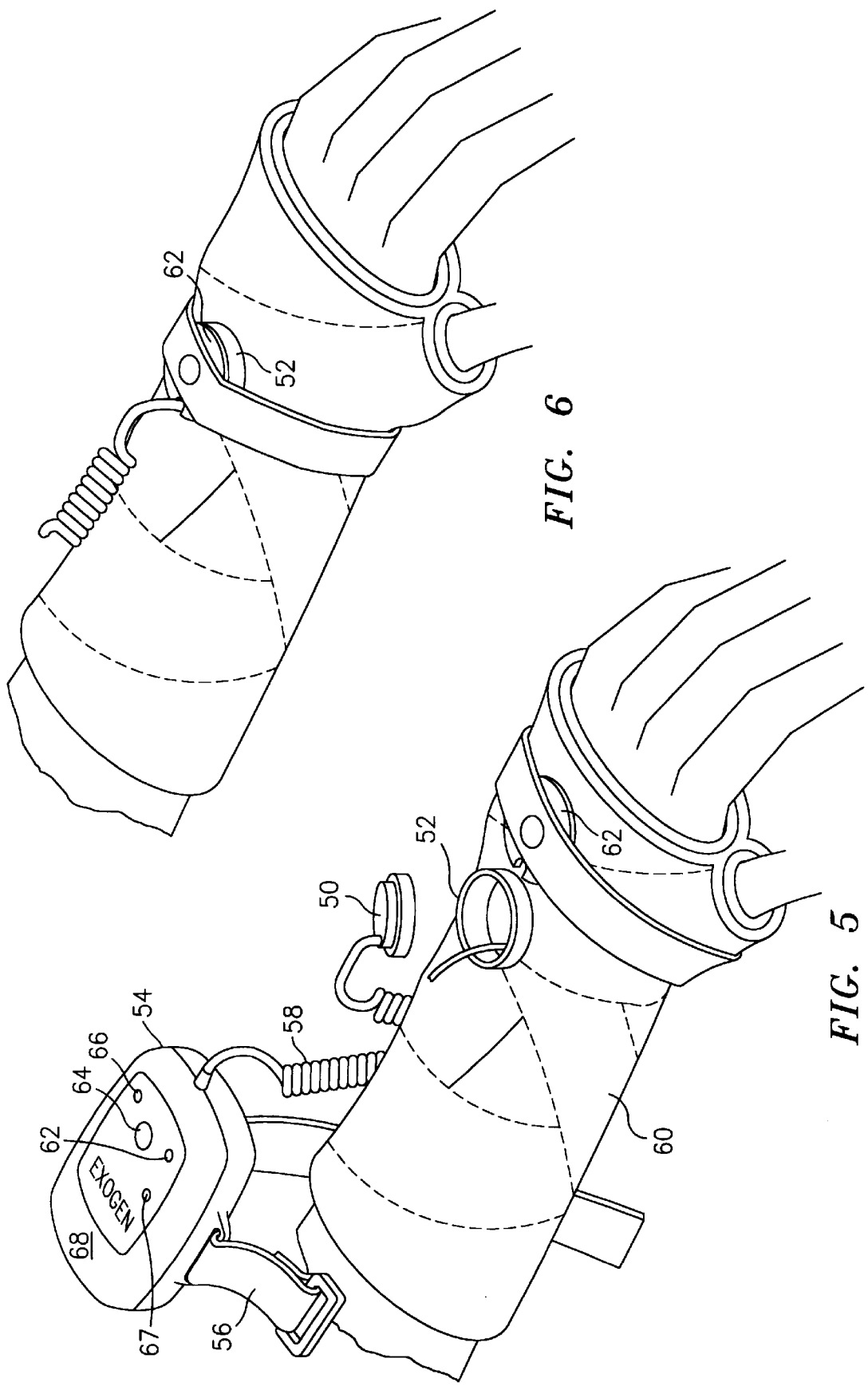
FIG. 5 shows the ultrasonic transducer head prior to installation within an insert which is mounted in a cast.
FIG. 6 shows the transducer head installed in the insert and secured by a cover.

FIG. 5 and 6 show a preferred embodiment of the controller in practical use. The processor 16, output driver 18, battery 30, sensing circuit 12 and related circuitry (not shown in FIGS. 5 and 6) can all be assembled into housing 54. A "GEL" alarm 62, a "BAT LOW" alarm 66 and a compliance indicator 67 can be positioned on top of the housing 54 in plain view of the patient. Also, a power button 64 can be located on the housing for easy access by the patient. FIG. 5 shows the ultrasonic transducer head 50 prior to installation within an insert 52 which is mounted in a cast 60. The unit 68 can be secured to the patient by straps 56. A flexible cable 58 can be used to connect the unit 68 to transducer head 50. FIG. 6 shows the transducer head 50 installed in the insert 52 and secured by a cover 62. The insert 52 and therefore the transducer head 50 are located over the injured area and the ultrasound conductive material (not shown) is placed between the transducer head 50 and the patients skin.

In other embodiments, unit 68 is configurable into different housings. Ultrasonic transducer controller 10 (FIG. 1) may be included within commercially available devices, for example an SAFHS 2000 available commercially from Exogen, Inc, Piscataway, N.J. Ultrasonic transducer controller 10 (FIG. 1) may be configured with appropriate inputs and outputs to work with or control the SAFHS 2000 unit in accordance with the present invention.

Figure 7:
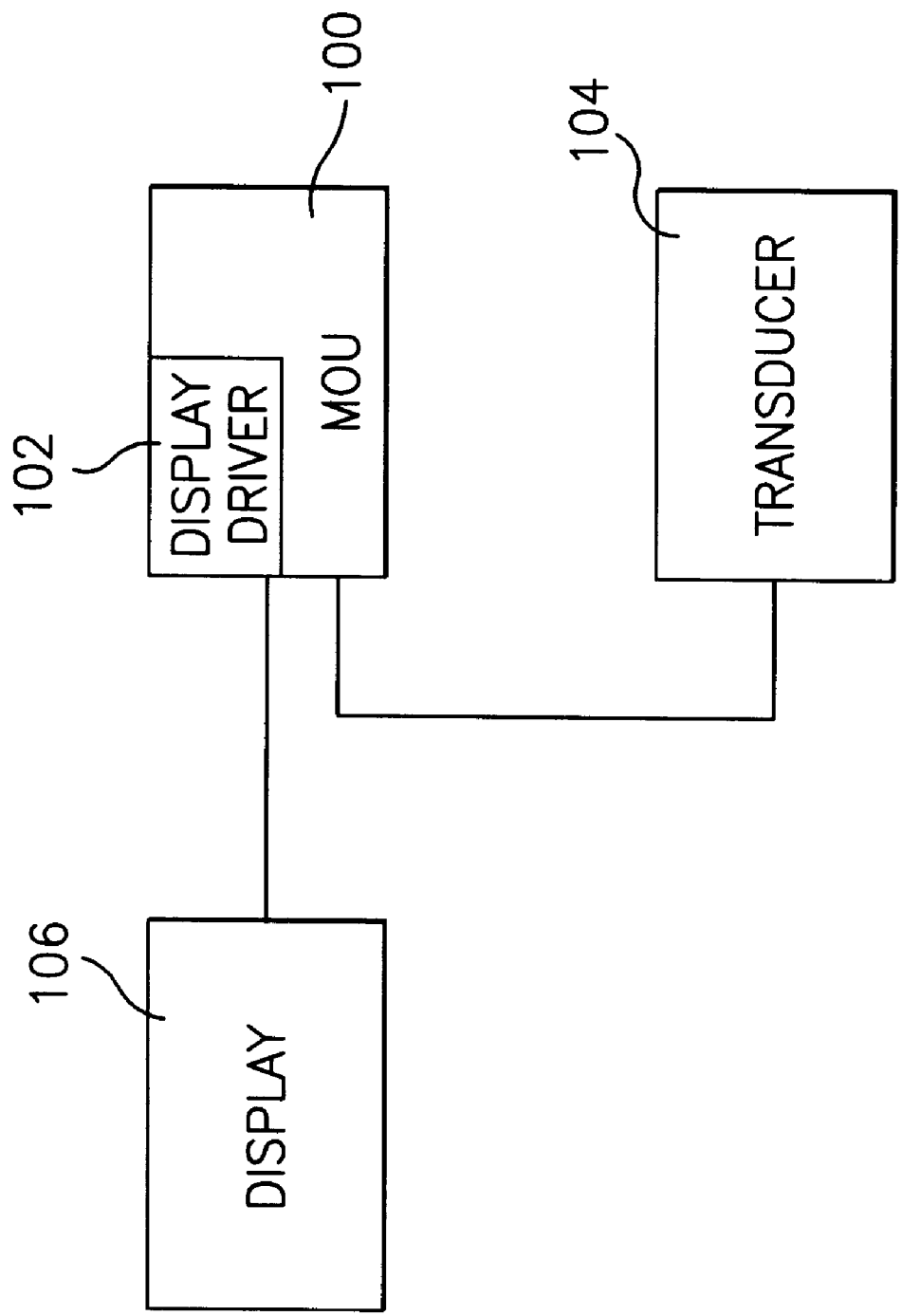
FIG. 7 is a block diagram of a controller having a display driver therein for driving a display.

The microprocessor of the present invention is also contemplated for use in passivation of the battery power supply. Lithium batteries, while exhibiting long shelf life, on the order of about 8 years are subject to oxide buildup which increases the internal resistance of the battery. When the internal resistance increases to a point where there is insufficient current to drive the controller, the unit will not function. In one embodiment, the microprocessor senses this oxide layer buildup, also referred to as the passivation layer, and applies a resistance less than the resistance of the controller to effectively burn off at least a portion of the passivation layer thus permitting full operation of the controller without the need to replace the battery. Further, the microprocessor can be provided with two clock circuits with one circuit assigned to time keeping and the other circuit activating the processor at a reduced power level on a periodic basis to clear the passivation layer. For example, the processor could be activated once a day to run for about 5 seconds at a power level of 100 mA. This step keeps the battery chemistry in good operating condition and maximizes useful battery life. 10 The main operating unit is configurable for use with other devices. Referring to FIG. 7, a preferred embodiment of a main operating unit 100 includes a liquid crystal display (LCD) interface board or display driver 102. A transducer 104 connects to unit 100 where feedback is processed and transferred to board 102 and output to a liquid crystal display 106. Display 106 is preferably mounted on unit 100. Information displayed on display 106 includes treatment time elapsed or remaining, number of days left in the treatment regimen, warnings or error messages, etc.

Figure 8:
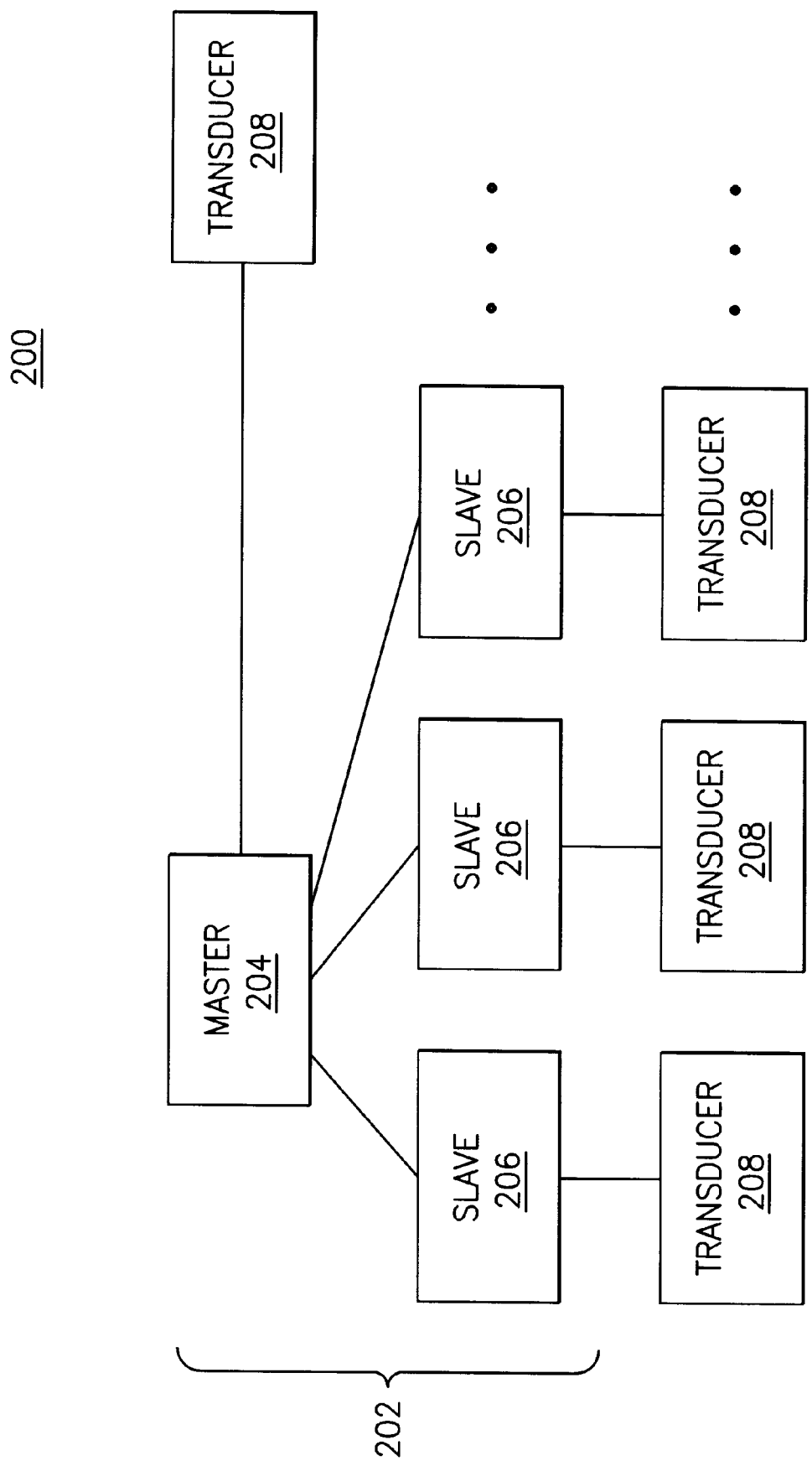
FIG. 8 is a block diagram showing an ultrasound delivery controller system for driving ultrasonic transducers includes a plurality of controller boards.

Referring to FIG. 8, a plurality of controller boards 202 may be included in a main operating unit 200. A master board 204 is included and comprises circuitry for controlling, synchronizing and or sequencing slave boards 206. Each board controls outputs to a transducer 208. Transducers 208 may be positioned about a treatment site to form an array of transducers appropriately located to better treat an injury, for example at different locations about a patient's thigh to treat a tibia. Transducers 208 are sequenced so as to minimize interference between ultrasound waves supplied by each transducer. To apply ultrasound to the treatment site, master board 204 supplied time shifted enable signals to slave boards 206 to provide time staggering treatment delivery from different transducers. In a preferred embodiment, time shifts between transducers are between about 200 microseconds to about 800 microseconds.

Having described preferred embodiments of a novel processor control device (which are intended to be illustrative and not limiting), it is noted that modifications and variations can be made by persons skilled in the art in light of the above teachings. It is therefore to be understood that changes may be made in the particular embodiments of the invention disclosed which are within the scope and spirit of the invention as defined by the appended claims. Having thus described the invention with the details and particularity required by the patent laws, what is claimed and desired protected by Letters Patent is set forth in the appended claims.

What is claimed is:

1. A controller for driving an ultrasonic transducer comprising:
   a processor, responsive to a feedback signal, for generating control signals;
   an output driver, responsive to the control signals, to cause the ultrasonic transducer to generate ultrasound having a power level corresponding to the control signal; and
   means for sensing an amount of ultrasound conductive material associated with the ultrasonic transducer, and for generating the feedback signal therefrom.

2. The controller of claim 1, wherein the means for sensing includes a gel sensing circuit, responsive to a resistance associated with the amount of ultrasound conductive gel, for sensing the amount thereof and for generating the feedback signal corresponding to the resistance.

3. The controller of claim 2 wherein:
   the output driver includes a first electrical contact;
   the gel sensing circuit includes a second electrical contact, wherein the resistance is detected between the first and second contacts.

4. The controller of claim 3 wherein the first and second electrical contacts are disposed substantially adjacent to an operative surface of the ultrasound transducer with the ultrasound conductive gel disposed thereon.

5. The controller of claim 1 wherein:
   the feedback means outputs the feedback signal to an input port of the processor; and
   the processor includes an analog-to-digital converter connected to the input port for digitizing the feedback signal for use in generating the control signals.

6. The controller of claim 1 further comprising:
   a memory; and
   the processor includes:
      means for timing the generation of the ultrasound by the ultrasound transducer to generate timing data to be stored in the memory as patient compliance data.

7. The controller for driving an ultrasonic transducer as recited in claim 1 wherein said means for sensing an amount of ultrasound conductive material comprises a receiver for receiving a reflected ultrasound signal and means for disabling the controller if no reflected signal is received.

8. The controller for driving an ultrasonic transducer as recited in claim 1 further comprises a switching regulator for adjustably converting a supply voltage to the output driver to increase the input voltage to the output driver during treatment.

9. The controller for driving an ultrasonic transducer as recited in claim 1 further comprises a CMOS digital buffer connecting to a field effect transistor of the output driver such that control signals to a gate of the field effect transistor are conditioned to reduce power loss during on and off switching of the field effect transistor.

10. The controller for driving an ultrasonic transducer as recited in claim 1, further comprises a display driver to provide a visual image of treatment information to a display.

11. A controller for driving an ultrasonic transducer comprising:
   a processor, responsive to a feedback signal, for generating control signals; and
   the processor further includes
      a memory,
      means for timing data to be stored in the memory,
      a comparing device for comparing timing data to predetermined levels, such that the processor is disabled if data is not in compliance;
   an output driver, responsive to the control signals, to cause the ultrasonic transducer to generate ultrasound having a power level corresponding to the control signal; and
   a gel sensing circuit, responsive to a resistance associated with the amount of ultrasound conductive gel, for sensing the amount thereof and for generating the feedback signal corresponding to the resistance.

12. The controller of claim 11, further comprising a stored energy device for supplying power to the controller.

13. The controller of claim 11, further comprising a memory having an erasable code;

means for inputting a code, a comparing device for comparing an input code with the stored code such that when the codes match the processor is enabled.

14. The controller of claim 13, wherein:

the means for inputting code is a battery.

15. The controller as recited in claim 11 further comprises a switching regulator for adjustably converting a supply voltage to the output driver to increase the input voltage to the output driver during treatment.

16. The controller for driving an ultrasonic transducer as recited in claim 11, further comprises a CMOS digital buffer connecting to a field effect transistor of the output driver such that control signals to a gate of the field effect transistor are conditioned to reduce power loss during on and off switching of the field effect transistor.

17. The controller as recited in claim 11 wherein the gel sensing circuit comprises a receiver for receiving a reflected ultrasound signal and means for disabling the controller if no reflected signal is received.

18. The controller as recited in claim 11, further comprises a display driver to provide a visual image of treatment information to a display.

19. A controller for driving an ultrasonic transducer comprising:

a processor, responsive to a feedback signal, for generating control signals;

the processor further includes a memory, at least one analog-to-digital convertor for digitizing timing and input data, a comparing device for comparing timing data to predetermined values, such that the processor is disabled if data is not in compliance;

an output driver, responsive to the control signals, to cause the ultrasonic transducer to generate ultrasound having a power level corresponding to the control signal; and a gel sensing circuit, responsive to a resistance associated with the amount of ultrasound conductive gel, for sensing the amount thereof and for generating the feedback signal corresponding to the resistance.

20. A controller for driving an ultrasonic transducer as recited in claim 19 further comprising:

a housing for storing the processor, the memory, the at least one analog-to-digital convertor, the comparing device, the output driver, and the gel sensing circuit;

the housing including a securing means for mounting on a patient and connected to a cable for sending and receiving signals of the ultrasonic transducer.

21. An ultrasound delivery controller system for driving ultrasonic transducers comprising:

a plurality of controller boards, each board for controlling an ultrasound transducer wherein one of the plurality of boards is a master board for controlling and sequencing the other boards;

each board further comprising a processor, responsive to a feedback signal, for generating control signals;

an output driver, responsive to the control signals, to cause the ultrasonic transducer to generate ultrasound having a power level corresponding to the control signal; and means for sensing an amount of ultrasound conductive material associated with the ultrasonic transducer, and for generating the feedback signal therefrom.

22. The ultrasound delivery controller system as recited in claim 21, wherein the transducers are arranged in an array about a treatment site, the transducers being sequenced by the master board to provide ultrasound treatment at staggered times.

* * * * *